United States Patent
Watkins et al.

(10) Patent No.: US 6,241,948 B1
(45) Date of Patent: Jun. 5, 2001

(54) SENSING DEVICE WITH SOL-GEL DERIVED FILM ON THE LIGHT SOURCE

(75) Inventors: A. Neal Watkins, Beavercreek, OH (US); Brett R. Wenner, Lexington, KY (US); Jeffrey D. Jordan, Beavercreek, OH (US); Frank V. Bright, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/082,235

(22) Filed: May 20, 1998

(51) Int. Cl.[7] .................................................. G01N 21/64

(52) U.S. Cl. ................................... 422/82.05; 422/82.08; 356/436; 356/437; 257/98

(58) Field of Search ............................. 422/82.04, 82.08, 422/82.09, 82.05; 436/136, 137; 356/244, 246, 436, 437; 257/95, 98, 99, 100

(56) References Cited

U.S. PATENT DOCUMENTS

| | | | |
|---|---|---|---|
| 4,752,447 | * 6/1988 | Kimmel et al. | 422/56 |
| 4,863,694 | * 9/1989 | Kimmel et al. | 422/86 |
| 5,489,988 | 2/1996 | Ackley et al. | |
| 5,517,313 | 5/1996 | Colvin, Jr. | |
| 5,629,533 | 5/1997 | Ackley et al. | |
| 5,650,331 | * 7/1997 | Jorgensen et al. | 436/163 |

OTHER PUBLICATIONS

A. Neal et al., Portable, Low–Cost, Solid–State Luminescence–Based O2 Sensor, Applied Spectroscopy 56/5, pp. 750–754 May 1998.*

Bergman, "Rapid–Response Atmospheric Oxygen Monitor Based On Fluorescent Quenching," Nature, 218:396 (1968).

Watts et al., "Spectroscopic Characterization of Complexes of Ruthenium and Iridium (III) with 4,4'–Diphenyl–2, 2'–Bypyridine and 4,7–Diphenyl–1, 10–phenanthroline[1,]," Journal of the American Chemical Society 93:3184–3188 (1971).

Lin et al., "Mechanism of the Quenching of the Emission of Substituted Polypyridineruthenium (II) Complexes by Iron (III), Chromium (III), and Europium (III) Ions," Journal of the American Chemical Society, 98:6536 (1976).

Buell et al., "Heterogeneous Preparation of Singlet Oxygen Using an Ion–Exchange–Resin–Bound Tris (2, 2'–bipyridine) Ruthenium (II) Photosensitizer," J. Phys. Chem, 87:4675 (1983).

Kroneis et al., "A Fluorescence–Based Sterilizable Oxygen Probe for Use in Bioreactors," Sensors and Actuators, 4:587 (1983).

Lakowicz, "Quenching of Fluorescence," Principles of Fluorescence Spectroscopy, New York, NY:Plenum Press, Chapter 9, pp. 257–301 (1983).

Peterson et al., "Fiber–Optic Probe for in Vivo Measurement of Oxygen Partial Pressure," Anal. Chem., 56:62 (1984).

(List continued on next page.)

Primary Examiner—Robert J. Warden, Sr.
Assistant Examiner—Kaj K. Olsen
(74) Attorney, Agent, or Firm—Nixon Peabody LLP

(57) ABSTRACT

A sensing system for quantifying a gaseous species or an analyte in a sample in accordance with one embodiment of the present invention includes a light emitting diode and a detector. The light emitting diode is coupled to a power source and at least a portion of the light emitting diode is coated with a sol-gel-derived film doped with a doping material. The detector is spaced from and substantially across from the portion of the light emitting diode coated with the sol-gel-derived film. The system may include a filter which is located between the light emitting diode and the detector and a processing system which is coupled to the detector for quantifying the amount of a gaseous species or an analyte in a sample based on data from the detector.

21 Claims, 4 Drawing Sheets

OTHER PUBLICATIONS

Wolfbeis et al., "Fiber Optical Fluorosensor for Determination of Halothane and/or Oxygen," *Anal. Chem.*, 57:2556 (1985).

Bacon et al., "Determination of Oxygen Concentrations by Luminescence Quenching of a Polymer–Immobilized Transition–Metal Complex," *Anal. Chem.*, 59:2780 (1987).

Sharma et al., "Fiberoptic Oxygen Sensor Based on Fluorescence Quenching and Energy Transfer," *Applied Spectroscopy*, 42(6):1009 (1988).

Atkins, "Changes of State: Physical Transformations of Simple Mixtures," *Physical Chemistry*, $4^{th}$ ed., New York, NY:W.H. Freedman and Company, Chapter 7, pp. 154–183 (1990).

Carraway et al., "Photophysics and Photochemistry of Oxygen Sensors Based on Luminescent Transition–Metal Complexes," *Anal. Chem.*, 63:337 (1991).

Eftink, "Fluorescent Quenching: Theory and Applications," *Topics in Fluorescence Spectroscopy*, vol. 2, New York, NY:Plenum Press, Chapter 2, pp. 53–127 (1991).

Sacksteder et al., "Design of Oxygen Sensors Based on Quenching of Luminescent Metal Complexes: Effect of Ligand Size on Heterogeneity," *Anal. Chem.*, 65:3480 (1993).

Klimant et al., Novel Metal–Organic Ruthenium (II) Diimin Complexes for Use as Longwave Excitable Luminescent Oxygen Probes, *Talanta*, 41(6):985 (1994).

MacCraith et al., "LED–based Fibre Optic Oxygen Sensor using Sol–gel Coating," *Electronics Letters*, 30(11):888 (1994).

Dave et al., "Sol–Gel Encapsulation Methods for biosensors," *Anal. Chem.*, 66(22):1120A (1994).

MacCraith et al., "Light–emitting–diode–based Oxygen Sensing Using Evanescent Wave Excitation of a Dye–doped Sol–gel Coating," *Optical Engineering*, 33(12):3861 (1994).

Demas et al., "Design and Applications of Highly Luminescent Transition Metal Complexes," Lakowicz, ed., *Topics in Fluorescence Spectroscopy*, vol. 4, New York, NY:Plenum Press, Chapter 4, pp. 71–107 (1994).

Xu et al., "Oxygen Sensors Based on Luminescence Quenching: Interactions of Metal Complexes with the Polymer Supports," *Anal. Chem.* 66(23):4133 (1994).

Hartmann et al., "Luminescence Quenching Behavior of an Oxygen Sensor Based on a Ru(II) Complex Dissolved in Polystyrene," *Anal. Chem.* 67(1):88 (1995).

Lev et al., "Organically Modified Sol–Gel Sensors," *Anal. Chem.*, 67(1):22A (1995).

Demas et al., "Modeling of Luminescence Quenching–Based Sensors: Comparison of Multisite and Nonlinear Gas Solubility Models," *Anal. Chem.*, 67(8):1377 (1995).

Chung et al., "Measurement of Dissolved Oxygen in Water Using Glass–Encapsulated Myoglobin," *Anal. Chem.*, 67(9):1505 (1995).

Klimant et al., "Oxygen–Sensitive Luminescent Materials Based on Silicone–Soluble Ruthenium Diimine Complexes," *Anal. Chem.*, 67(18):3160 (1995).

Xu et al., "Oxygen Sensors Based on Luminescence Quenching: Interactions of Pyrene with the Polymer Supports," *Anal. Chem.*, 67(18):3172 (1995).

Papkovsky, "New Oxygen Sensors and their Application to Biosensing," *Sensors and Actuators B*, 29:213 (1995).

Murtagh et al., "Development of a Highly Sensitive Fibre Optic $0_2$/D0 Sensor Based on a Phase Modulation Technique," *Electronics Letters*, 32(5):477 (1996).

McEvoy et al., "Dissolved Oxygen Sensor Based on Fluorescence Quenching of Oxygen–sensitive Ruthenium Complexes Immobilized in Sol–Gel–derived Porous Silica Coatings," *The Analyst*, 121:785 (1996).

Jordan et al., "Aerosol–generated Sol–gel–derived Thin Films as biosensing Platforms," *Analytica Chimica Acta*, 332:83 (1996).

Draxler et al., "Time–resolved Fluorescence Spectroscopy for Chemical Sensors," *Applied Optics*, 35(21):4117 (1996).

Krihak et al., "Highly Sensitive, All Solid State Fibre Optic Oxygen Sensor Based on the Sol–gel Coating Technique," *Electronic Letter*, 32:240 (1996).

Ingersoll et al., "Using Sol–gel–based Platforms for Chemical Sensors," *Chemtech*, 27:26 (1997).

Lee et al., "Optical Sensor for Oxygen Using a Porphyrin–doped Sol–gel Glass," *The Analyst*, 122:81 (1997).

Demas et al., "Applications of Luminescent Transition Metal Complexes to Sensor Technology and Molecular Probes," *Journal of Chemical Education*, 74(6):690 (1997).

Jordan et al., "A Portable, Low Cost, Solid–State Luminescence–Based $O_2$ Sensor," *Applied Spectroscopy*, submitted (1997).

* cited by examiner

SENSING DEVICE WITH SOL-GEL DERIVED FILM ON THE LIGHT SOURCE

The U.S. Government has a paid-up license in this invention and the right in limited circumstances to require the patent owner to license others on reasonable terms as provided for by the terms of Grant No. CHE-9626636 awarded by the National Science Foundation and Grant No. N00149610501 awarded by the Office of Naval Research.

FIELD OF THE INVENTION

This invention relates generally to a sensor and, more particularly, to a sensor for the quantification of an analyte in a sample.

Throughout this application, references are cited by reference to endnotes which appear after the detailed description. The respective disclosure of each of these references is incorporated in its entirety by reference.

BACKGROUND OF THE INVENTION

The ability to quantify gaseous species, such as $O_2$ and $NH_3$, and analytes in solution, such as pH, $PO_2$, $PCO_2$, glucose, cholesterol, antigens, haptens, amino acids, and organic molecules, is important in industry, biomedicine, and the analytical sciences.

Traditionally, molecular oxygen, $O_2$, has been sensed using a device known as the Clark electrode. Although this electrode works, it has limitations including consumption of the $O_2$, relatively long response times, and the tendency of the electrode to become poisoned by contaminants, such as proteins and organics. As a result, other solutions, which rely upon optical sensing schemes for quantifying $O_2$, have been developed.[1-21]

Most optical sensing schemes are based on the quenching of a luminescent species by a gas, such as molecular oxygen.[1-11,22-24] In this approach, the $O_2$ dependence, or the dependence of any other quencher like Cl-, Br-, J-, $Cu^{2+}$, $Ni^{2+}$, $Cr^{2+}$, $Fe^{2+}$, $Fe^{3+}$, or acrylamide, on the emission intensity is described by the Stern-Volmer expression:[25,26]

$$\frac{I_0}{I} = 1 + K_{SV}[O_2] = 1 + k_q\tau_0[O_2]$$

where $I_0$ is the intensity in the absence of $O_2$, I is the intensity in the presence of $O_2$ at concentration $[O_2]$, $K_{SV}$ is the Stern-Volmer quenching constant, $k_q$ is the bimolecular quenching constant, and $\tau_0$ is the excited-state luminescence lifetime of the emissive species in the absence of $O_2$. Accordingly, by monitoring the luminescence intensity, the amount of $O_2$ present in a given sample can be determined.

Early optical sensing schemes used $O_2$ sensors which were based on the fluorescence from polycyclic aromatic hydrocarbons (PAHs) with long excited-state lifetimes, such as pyrene, benzo[a]pyrene, pyrenebutyric acid, and decacyclene.[1-5,11,12] Since these fluorophores have reasonably long excited-state lifetimes (to 400 ns), they are susceptible to $O_2$ quenching. Unfortunately, they also exhibit absorbance maxima in the ultraviolet or blue spectral region. As a result, the light sources in these optical sensing schemes consume significant electrical power and/or are expensive. Additionally, the detectors needed for these optical sensing schemes (e.g., photomultiplier tubes) are costly and require high voltage power supplies.

Other luminescent species that are susceptible to $O_2$ quenching include platinum and palladium porphyrin complexes[6-7], and ruthenium poly(pyridyl) complexes 8–10,14–15,17–21 Tris(4,7-diphenyl-1,10-phenanthroline)ruthenium(II), which is commonly referred to as [Ru $(dpp)_3]^{2+}$, is particularly attractive for $O_2$ sensing because it exhibits a high luminescent quantum yield, long excited-state lifetime, large Stokes shift, and strong absorption in the blue-green spectral region.[22-24, 27] These luminescent species have shown promise as luminescence quantum counters, as singlet oxygen generators[25,26] for synthetic applications, and as sensors and molecular probes.[29]

However, simple, small, and inexpensive optical sensing systems with these luminescent species have not yet been developed. The principal difficulties associated with constructing these sensing systems are with the immobilization of the $O_2$ responsive species and the relatively high cost of the excitation and detection system.

One approach to overcome these difficulties involves an optical $O_2$ sensor that uses a light emitting diode and a silica optical fiber with a sol-gel-derived film deposited on one surface.[17-21] The use of the sol-gel-derived film to entrap species provides a number of advantages including: (1) ambient processing conditions; (2) tunable film porosity; (3) good thermal stability; (4) optical transparency; and (5) simple dopant entrapment procedures.30–32 However, the use of the optical fiber adds to complexity and cost of the system and requires careful, precise, and costly manufacture to properly couple the light from the light emitting diode into the fiber and optically filter the fluorescence.

An alternative approach was recently described in U.S. Pat. No. 5,517,313 to Colvin, Jr., which is herein incorporated by reference. In this approach $[(Ru(dpp)_3]^{2+}$ is immobilized within a silicone:naptha membrane (1:2, vol:vol), and a light emitting diode is embedded directly into the membrane. In this configuration, the housing for the light emitting diode acts essentially as a waveguide to couple the light into the film. This configuration is optically simpler than the aforementioned optical fiber design,[17-21] but still requires complicated flow cell and waveguide construction techniques for proper operation.

SUMMARY OF THE INVENTION

A sensing system for quantifying an analyte in a sample in accordance with one embodiment of the present invention includes a light source and a detector. The light source is coupled to a power source, and at least a portion of the light source is coated with a sol-gel-derived film doped with a doping material, such as a ruthenium complex. The detector is substantially across from and is separated by an open space from the portion of the light source coated with the sol-gel-derived film. The system may further include a filter which is located between the light source and the detector and a processing system which is coupled to the detector for quantifying the amount of analyte that is present in the sample based on data from the detector.

A sensing apparatus in accordance with another embodiment of the present invention includes a housing, a light source, a sol-gel-derived film, and a detector. The housing has an inlet for receiving a sample and an outlet for discharging the sample. The light source is coupled to a power source and is positioned in the housing between the inlet and the outlet. A sol-gel-derived film doped with a doping agent is deposited on at least a portion of the light source. The detector is spaced from and located substantially across from the portion of the light source coated with the sol-gel-derived film. The sensing apparatus may include a processing system which is coupled to the detector for processing data detected by the detector.

The present invention also relates to a method for quantifying an analyte in a sample. The method includes providing a light source which is coupled to a power source and on at least a portion of which is coated a sol-gel-derived film doped with a doping material. The sol-gel-derived film doped with the doping material is contacted with the analyte that is present in the sample. Light from the light source coated with the sol-gel-derived film doped with the doping material is transmitted through the sample towards the detector where it is detected.

One of the advantages of the present invention is the simplicity of its design when compared to prior designs. As discussed above, the sensing system can be easily constructed with an inexpensive light emitting diode, a low cost filter, and a low cost photodiode.

Another advantage of the present invention is that it consumes smaller amounts of electrical power than prior systems. As a result, the sensing system can be battery operated which makes it much more portable and also less expensive to operate.

Yet another advantage of one of the embodiments of the invention is the fast response times, good reversibility, and detection limits of 0.02% and 110 ppb, respectively, for $O_2$ in gaseous and aqueous samples that the sensing system can provide when ruthenium complex of tris(4,7-diphenyl-1,10-phenanthroline)ruthenium(II) ($[Ru(dpp_3)]^{2+}$) is immobilized within a porous sol-gel-derived film and cast directly onto the surface of light emitting diode. Thus, this sensing system provides a cost effective alternative to traditional electrochemical-based $O_2$ sensing and also provides a platform for other optically-based sensors.

Yet another advantage of the sensing system of the present invention is its ability to operate in both a gaseous phase and an aqueous phase. As a result, the sensing system is much more versatile than prior sensing systems.

DETAILED DESCRIPTION

Figure 1:
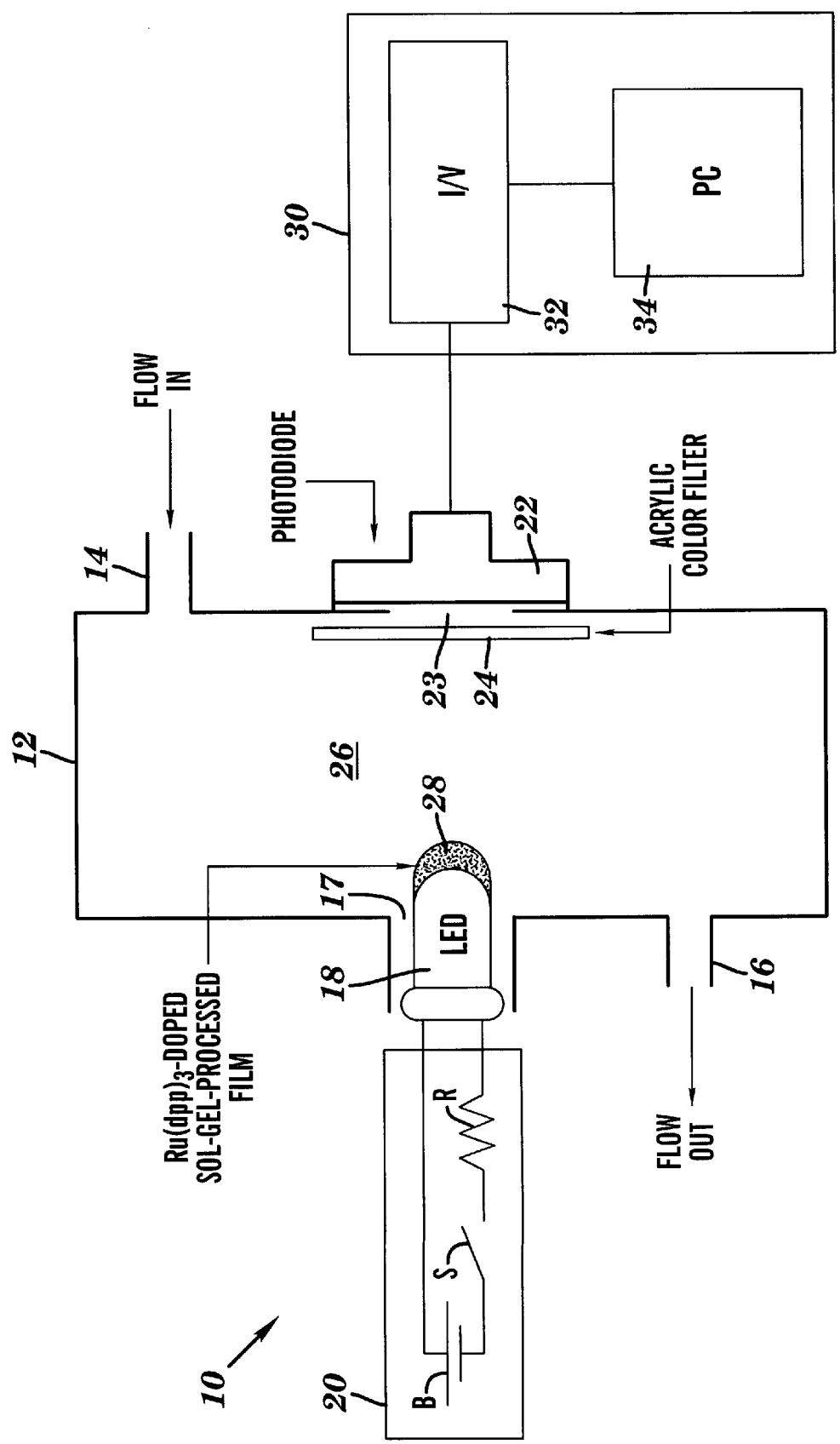
FIG. 1 is a partial schematic and a partial block diagram of a sensing system in accordance with one embodiment of the present invention.

A sensing system 10 for quantifying a species or an analyte in a sample in accordance with one embodiment of the present invention is illustrated in FIG. 1. The sensing system 10 includes a light source 18 which is at least partially coated with a sol-gel-derived film 28 doped with a doping material. Sensing system 10 also includes a detector 22 which is located substantially across from and is separated by an open space 26 from the portion of the light source 18 coated with the sol-gel-derived film 28.

FIG. 1 also illustrates a method in accordance with another embodiment of the present invention. The method includes the steps of providing a light source 18 and a detector 22, typically separated by an open space 26. At least a portion of the light source 18 is coated with a sol-gel-derived film 28 doped with a doping material. The present invention has a number of advantages including providing a sensing system 10 which has low power requirements, is small, portable, and stable, and is inexpensive to manufacture and operate.

Referring more specifically to FIG. 1, one particular embodiment of the sensing system 10 is illustrated. In this particular embodiment, the sensing system 10 includes a housing or chamber 12 with an inlet 14 and an outlet 16. The direction of flow through the housing 12 of a sample to be quantified is illustrated by the arrows at the inlet 14 and outlet 16. One of the advantages of the present invention is that the sensing system 10 can accommodate both gaseous and aqueous samples.

A light source 18, such as a light emitting diode or more specifically a blue quantum well light emitting diode, is positioned between the inlet 14 and the outlet 16, for example, in an opening 23 of the housing 12. Although, in this particular embodiment, the light source 10 is a light emitting diode from Nichia America, Corp. (part No. NSPB500S), other diodes having a transparent window can be used. Furthermore, although a light emitting diode is illustrated as the light source 18, other types of light sources 18, such as a diode laser, radioactive scintillator, chemiluminescent agent, or phosphorescent agent, can be used. The light source 18 is coupled to a power source 20, such as, a three 1.5 V batteries B in this particular example, although other types of power sources 20 can be used. One of the advantages of the present invention is that the sensing system 10 has low power requirements permitting it to be run on batteries. As a result, the sensing system 10 can be made compact and portable. Power source 20 can be coupled to a switch S and a resistor R to control the operation of light source 18.

A sol-gel-derived film 28 is deposited on a portion of the light source 18 which is in the housing 12. The sol-gel-derived film 28 is doped with a doping material or agent. In this particular embodiment, the doping material is a ruthenium complex, such as tris(4,7-diphenyl-1,10-phenanthroline)ruthenium(II), or $[Ru(dpp)_3]^{2+}$. Because it exhibits a high luminescent quantum yield, long excited-state lifetime, large Stokes shift, and strong absorption in the blue-green spectral region, $[Ru(dpp)_3]^{2+}$ is particularly well suited for detecting oxygen.

More particularly, in this particular embodiment, the sol-gel-derived film 28 is an $[Ru(dpp)_3]^{2+}$-doped aerosol-derived sol-gel-derived film which is prepared from the following reagents: tetraethylorthosilicate (TEOS) (also known as tetraethoxysilane) (available from United Chemical Technologies, Inc., hydrochloric acid (available from Fisher Scientific), tris(4,7-diphenyl-1,10-phenanthroline)ruthenium(II) dichloride (which can be prepared by conventional methods, such as those described in Demas et al., *J. Am. Chem. Soc.*, 93:3184 (1971), which is hereby incorporated by reference) and absolute ethanol (available from Pharmco). In this example, all of the reagents were used as received without further purification and all aqueous solutions were prepared with doubly-distilled deionized water. Of course, as one skilled in the art will recognize, other tetraalkoxysilanes or mixtures of tetraalkoxysilanes and organically modified silanes or alkylsilanes can be used in place of some or all of the tetraethoxysilane in the above procedure. In addition, other mineral acids can be used in place of the hydrochloric acid, and other alcohols can be used in place of ethanol.

To make the film 28 and then deposit it on the light source 18, a sol-gel-derived stock solution of TEOS, ethanol, water, and HCl in the molar ratios of about $1:2:2:10^{-4}$, respectively, is first prepared. The TEOS and ethanol are then added to a mixing vial and are magnetically stirred for approximately one minute. Next, the water/HCl mixture is added slowly to the TEOS/ethanol mixture dropwise with constant stirring. Once the water/HCl mixture has been added, the mixing vial of stock is sealed and allowed to stir at ambient conditions for six hours.

Meanwhile, the surface or surfaces of the light source 18 to receive the sol-gel-derived film 28 are cleaned by treating them with concentrated base, such as by soaking them in concentrated aqueous KOH solutions. After about one hour, the surfaces of the light source 28 are rinsed with copious amounts of water and allowed to dry under ambient conditions before further use.

Next, the $[Ru(dpp)_3]^{2+}$-doped sol-gel-derived film 28 is deposited on the light source 18 using, for example, an aerosol deposition technique, such as the ones described in Jordan et al., *Anal. Chim. Acta,* 332:83 (1996) and applicants' copending U.S. patent application Ser. No. 08/752,460, filed Nov. 18, 1996, which are hereby incorporated by reference. After the $[Ru(dpp)_3]^{2+}$-doped sol-gel-derived film 28 has been deposited, the coated light source 18 is kept in the dark and allowed to cure overnight under ambient conditions before it is ready for use in the sensing system 10.

The coated light source can be positioned entirely or partially with housing 12, so long as at least a portion of the coated surface of light source 18 is exposed to the interior of housing 12. In a preferred embodiment the coated light source is located adjacent an opening 17 in the housing 12, more preferably with only the coated portion of light source 18 exposed to the interior of housing 12.

A detector 22, such as a photodiode, preferably positioned adjacent another opening 23 in the housing 12, is located opposite from the light source 18 and separated from light source 18 by an open space 26. In this particular embodiment, the detector 22 is a silicon photodiode from Edmund Scientific (stock # P53,377) and is spaced about 0.5 cm from the sol-gel-derived film 28 on the light source 18. Although a photodiode is shown as the detector 22, other types of detectors, such as a photomultiplier tube, microchannel plate photomultiplier tube, photo tube, diode array, or any type of two dimensional array detector, can be used. Generally, the detector 22 is selected so that it is able to detect the emissions from the light source 18 with the sol-gel-derived film 28. As explained below, these emissions can be the emissions from the doping material in film 28 that is excited by light source 18 (in the case where the doping material fluoresces when excited by light from the light source 18), or they can be the emissions of the light source 18 itself (in the case where the doping material absorbs the light from the light source 18).

As illustrated in FIG. 1, a filter 24 can be located between the light source 18 with the sol-gel-derived film 28 and the detector 22. The filter is used to filter out the excitation light. In this particular embodiment, the filter is an acrylic color filter, although other types of filters, such as a glass and/or fused silica filter of any type, a prism, gratings or a monochromator, could be used. The filter is preferably selected so that it transmits the light emitted from the doping material (in the case where the doping material fluoresces) or the light source (in the case where the doping material absorbs from the light source) and absorbs other frequencies of light. Where the doping material is a fluorescent material, the filter is preferably selected so that it absorbs the frequencies of light used to excite the doping material.

In the embodiment illustrated in FIG. 1, the detector 22 is coupled to a processing system 30 which includes a current-and-voltage (I/V) meter 32 and a personal, programmable computer (PC) 34. The processing system 30 and the detector 22 are coupled to a power source not shown. The detector 22 transmits signals that are related (e.g., proportional) to the detected emissions to the current-and-voltage meter 32. The current-and-voltage meter 32 monitors these signals and provides current and/or voltage signals to the computer 34 regarding the detected emissions. The computer 34 includes a central processing unit (not shown) and a memory (not shown) which stores a program run by the central processing unit to analyze the detected emissions and quantify the amount of analyte in the sample. Processing systems and programs for analyzing data to quantify the amount of analyte in a sample are well known to those of ordinary skill in the art and thus will not be described in detail here.

Using the system illustrated in FIG. 1 to quantify the amount of an analyte in a sample, the sample is first passed into the housing 12 through the inlet 14. The sample being quantified can be gaseous or aqueous. The response time of the sensing system 10 is discussed below with reference to FIGS. 3 and 4. The sample passes between the light source 18 and the detector 22 and contacts the sol-gel-derived film 28 doped with a doping material. When switch S in power supply 20 is closed, light from the light source 18 coated with sol-gel-derived film 28 is transmitted through the sample towards the detector 22. Where a filter 24 is employed, it is positioned such that light from light source 18 coated with sol-gel-derived film 28 filters the light before it is detected by the detector 22.

For purposes of illustration, the following discussion assumes that the analyte is oxygen. In this case, the sensing system is constructed using a doping material that when exposed to oxygen, will exhibit a change in absorbance or fluorescence. The change can be one of intensity or wavelength or both. As indicated above, one example of a suitable doping material for detecting oxygen is a ruthenium complex (e.g., $[Ru(dpp)_3]^{2+}$). When the power source is activated light is emitted by the light source. The light is absorbed by the doping material, and, as a result, the doping material in the sol-gel-derived film is excited to an excited state. In the absence of oxygen, the doping material will fluoresce with an intensity $I_o$. If the sample contains oxygen, the oxygen will contact the doping material and quench the excited state of the doping material. As a result, the intensity of light (I) emitted from the doping material and transmitted across the housing 12 will be reduced. Consequently, the detector 22 will detect a change in the light from the light source 18 relative to the intensity of light in the absence of oxygen ($I_o$). The processing system 30 receives signals from the detector 22 regarding the change in intensity being detected and analyzes this data to quantify the amount oxygen in the solution using techniques well known to those of ordinary skill in the art. The sample then passes out of the housing 12 via the outlet 16.

Figure 2:
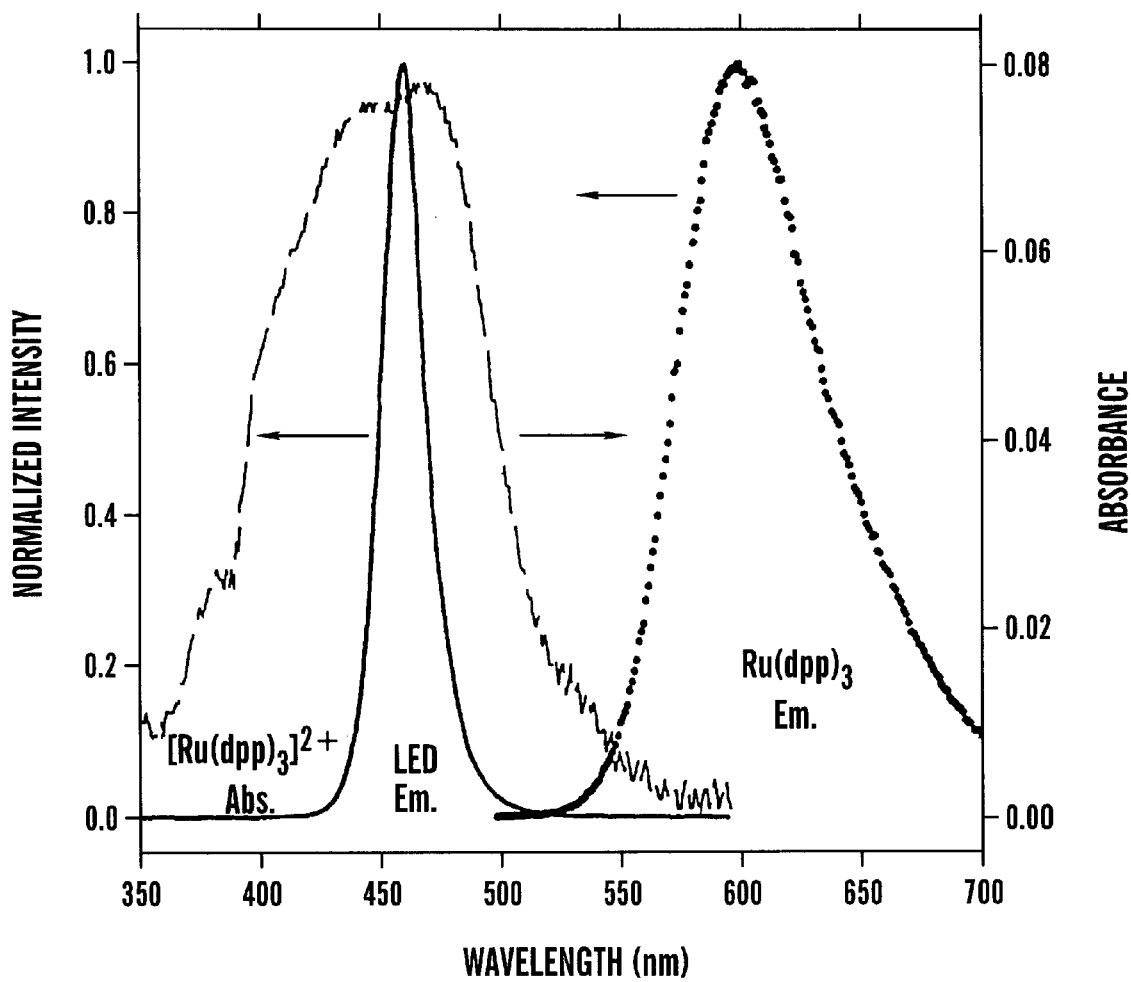
FIG. 2 is a graph comparing the normalized optical output from the Nichia brand light emitting diode illustrated by the straight line (—) with the $[Ru(dpp)_3]^{2+}$ absorbance illustrated by the dashed line (- - - -) and the $[Ru(dpp)_3]^{2+}$ normalized emission illustrated by the dotted line ( . . . )

Referring to FIG. 2, the absorbance spectra of $[Ru(dpp)_3]^{2+}$ within a sol-gel-derived film is illustrated by the dashed line (- - - -), the normalized emission spectra of $[Ru(dpp)_3]^{2+}$ within a sol-gel-derived-processed film is illustrated by the dotted line ( . . . ), and the normalized optical output profile of the light source 18, which in this particular example is the Nichia brand light emitting diode, is illustrated by the solid line (—). These spectra clearly illustrate that the LED optical output overlaps well with the

[Ru(dpp)$_3$]$^{2+}$ absorbance. It is also clear that there is little overlap between the LED optical output and the [Ru(dpp)$_3$]$^{2+}$ emission. As a result, a relatively inexpensive filter 24, such as a color acrylic filter, can be used to isolate the luminescence from the LED-generated excitation.

Figure 3:
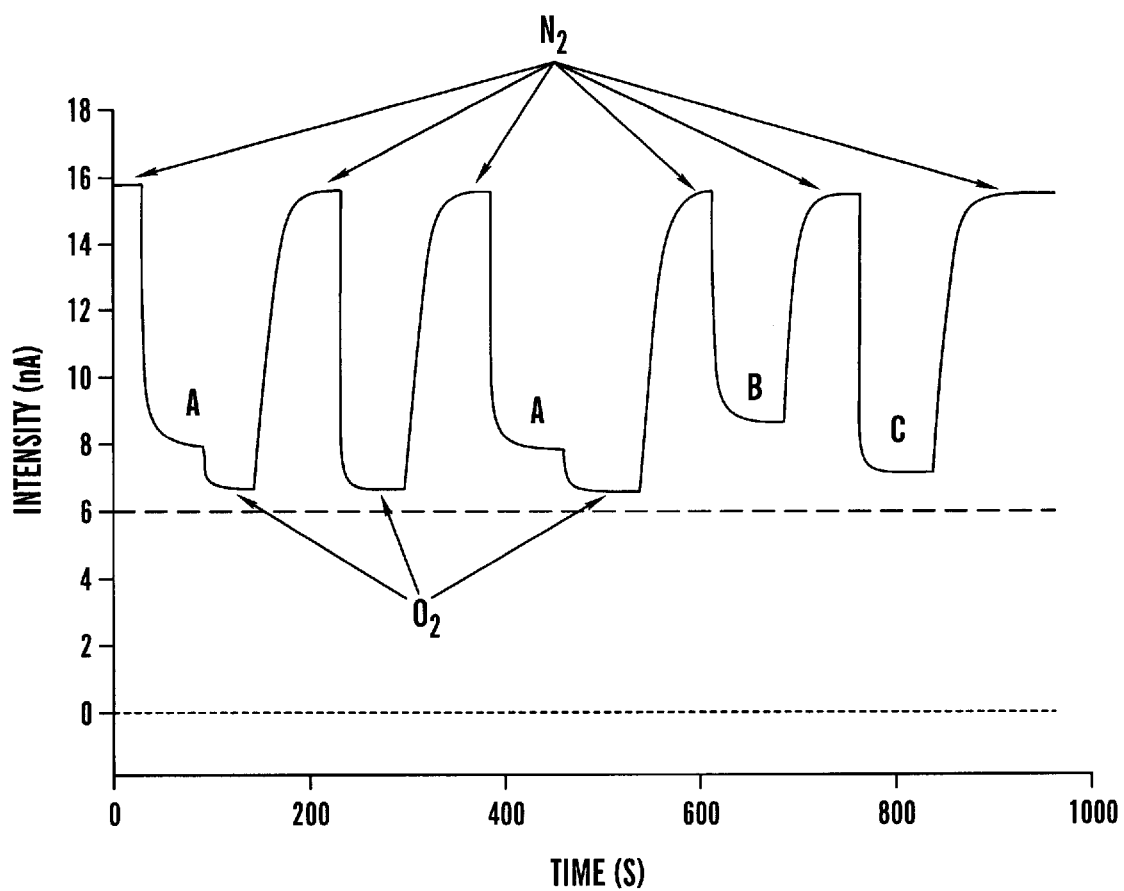
FIG. 3 is a graph illustrating a typical response of a sensing system in accordance with one embodiment of the present invention as a function of time for different gaseous mixtures.

Referring to FIG. 3, a typical gas phase response profile for the sensing system 10 to an atmosphere of N$_2$, O$_2$, and air is illustrated. The regions on the graph are denoted N$_2$ (pure nitrogen), O$_2$ (pure oxygen), A (pure air), B (a 1:1 air:N$_2$ mixture), and C (a 1:1 O$_2$:N$_2$ mixture). The longer dashed line (- - - -) is the response due to the output from the light source 18 leaking past the filter 24. The shorter dashed line (- - -) is the response when the output from the light source is blocked. The relatively low current readings arise from the fact that the photodiode being used as the detector 22 is operated in a photovoltaic mode (i.e., no external bias is applied to the photodiode). This response profile shows that it is characterized by excellent reversibility, a high degree of reproducibility, and a high signal-to-noise ratio (>500). As this graph illustrates, one of the advantages of this invention is its rapid response time. In this particular example, the uncorrected response time of the sensing system 10 (not accounting for the time required to flush the housing 12 and to manually switch the valves) is rapid, with a $t_{90}$ (the time required for 90% of the change in signal to occur) of about 3.5 s for going from N$_2$ to O$_2$, and about 30 s for going from O$_2$ to N$_2$.

Figure 4:
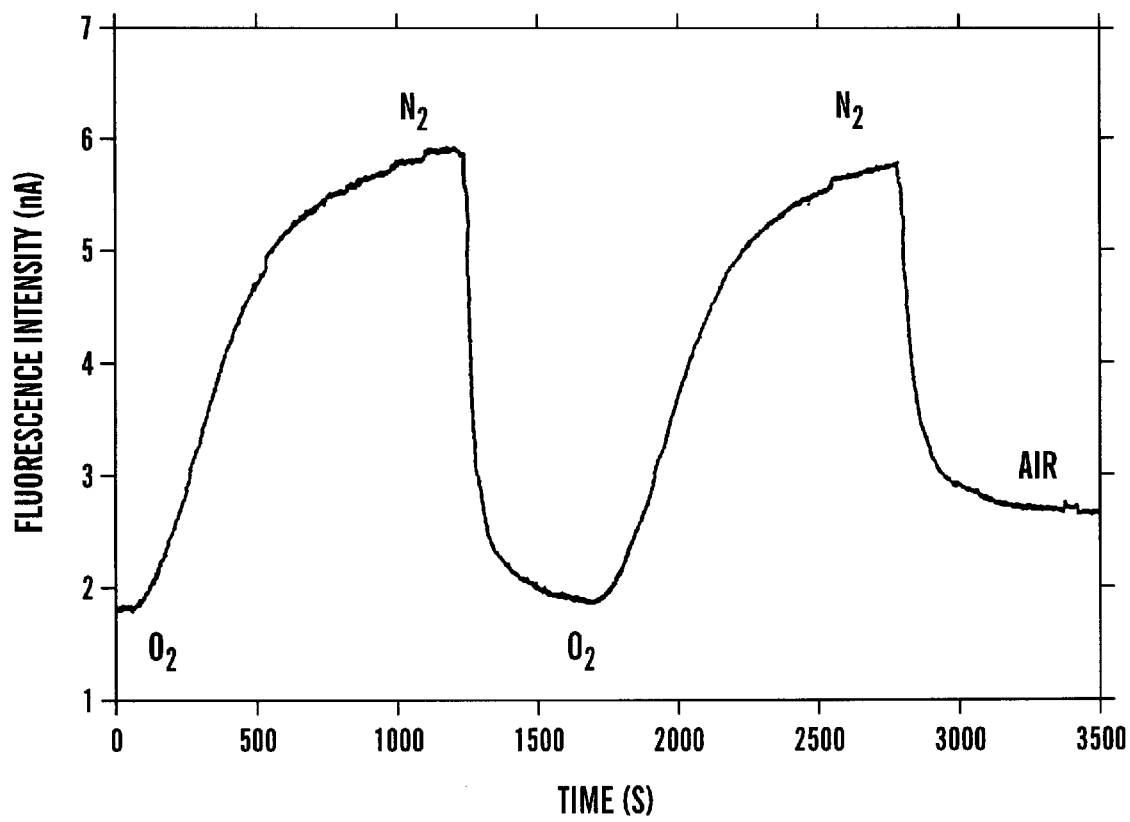
FIG. 4 is a graph of a typical response of the sensing system in accordance with the present invention to $O_2$-($O_2$), $N_2$-($N_2$), and air-saturated (Air) water.

FIG. 4 is a graph of the typical response profile for the sensing system 10 as it is subjected to N$_2$-, O$_2$-, and air-saturated water. In this particular example, the signal-to-noise ratio has decreased to about 100. This arises primarily because the optical collection efficiency within the housing or flow cell 12 decreases when a medium of high refractive index (water vs. air) is used between the light source 18 and the detector 22. This issue can be readily addressed in part by moving the light source 18 closer to the detector 22. A careful comparison of the results presented in FIG. 4 to those shown in FIG. 2, illustrate that the apparent response time of the sensing system 10 increases from about 4 s in the gas phase to nearer 3 min in water (N$_2$ to O$_2$) and from 30 s in the gas phase to about 10 min in water (O$_2$ to N$_2$). This increase in response time is most likely due to the significantly smaller rate of liquid water mass transport/exchange (compared to the gas phase) into and out of the sol-gel-derived film 28 on the light source 18. This slower water transport rate within the sol-gel-derived film 28 leads to a concomitant drop in analyte (O$_2$) transport to and from the doping material ([Ru(dpp)$_3$]$^{2+}$ molecules) which leads to a slower response time for O$_2$ measurements in aqueous media. Nevertheless, despite the slower response time, this experiment clearly demonstrates that the sensing system 10 can easily be used to monitor dissolved O$_2$ in liquids. Using Henry's Law to calculate the amount of O$_2$ present in each aqueous solution,[33] the detection limit of the sensing system 10 to dissolved O$_2$ is estimated to be about 110 ppb, which is comparable to detection limits determined using other solid-state optical based O$_2$ sensors.[20,21] It is also important to note that there was no detectable leaching of the ruthenium complex from the sol-gel-derived film 28 during our experiments nor any detectable change in luminescence that might be assigned to photon-induced decomposition or bleaching over prolonged, continuous measurements (days).

Accordingly, the use of solid-state electronics provides a viable means to develop advanced optically-based sensors from low cost components using simple construction techniques. The sensing system 10 provides a useful solid-state sensor platform for the detection and quantification Of O$_2$ in the gas phase and dissolved in liquids. The three second response time (for N$_2$ to O$_2$) and sensor precision are excellent for gas-phase sensing. The estimated detection limit is 0.02% O$_2$ in the gas phase. The sensor response time to O$_2$ dissolved in water is on the order of three minutes (again going from N$_2$ to O$_2$), the response is fully reversible, and the estimated limit of detection for dissolved O$_2$ is 110 ppb.

Although the sensing system 10 has been primarily illustrated and discussed with respect to using [Ru(dpp)$_3$]$^{2+}$ to sense molecular oxygen, the sensing system 10 can also be used with other doping materials. Generally, the doping material is one that is capable of absorbing light from the light source or that is capable of fluorescing when it is excited by light from the light source. The doping material is also preferably selected so that, when it is contacted with the analyte that is in the sample, its (i.e., the doping material's) ability to absorb light from the light source or to fluoresce when excited by light from the light source is increased, reduced or otherwise affected. One example of another doping material that can be used in the practice of the present invention is other ruthenium complexes, for example tris(bipyridyl)ruthenium, ReL (CO)$_3$ CNR$^+$ where L=2.2-bipyridine or 1,10-phenanthroline and R is test-Butyl of Ch$_3$(CH$_2$) or any other luminescent long lived organo-metallic complex. Like [Ru(dpp)$_3$]$^{2+}$, these ruthenium complexes are particularly effective for detecting the presence of gaseous oxygen in a gaseous sample or dissolved oxygen in a liquid (e.g., aqueous) sample. Another suitable doping material for use in the present invention is fluorescent or light absorbing oxidases that specifically recognize a particular analyte. For example, fluorescent or light absorbing glucose oxidase and cholesterol oxidase can be used to specifically recognize glucose and cholesterol, respectively. Yet another suitable doping material for use in the present invention includes fluorescent or light absorbing antibodies that specifically recognize a particular antigen. Antibody/antigen pairs are well known in the art and new ones are being developed continuously. All such antibodies, known and yet to be discovered, are viewed as being useful in the practice of the present invention. Such antibodies can be labeled with fluorescent fluorophores by conventional methods, such as those described in Bright, et al. Anal. Chem. 1990, 62, 1065–1069, which is hereby incorporated by reference. The antibody used as the doping material can recognize protein antigens, or it can be one that recognizes a drug or hapten. Other useful doping agents are light absorbing or fluorescent chelating agents whose light absorption or fluorescing properties change when they bind to one or more ions. Preferably, the chelating agent specifically binds to one and only one ion. For example, Fura 2, Indo-1, Quin-2, Rhod-2, Calcium Green, Calcium Orange, Calcium Crimson, Calcium Green 488 BAPTA, Fura Red, Calceine, and Calceine Blue (available from Molecular Probes) are fluorescent chelator that binds selectively to calcium ions, Mag-Fura-2, Mag-Fura-5, Mag-Indo-1, and fura-Red (available from Molecular Probes) bind Mg$^{2+}$, 5-sulfo-8-hydroxyquinoline binds selectively to zinc ions as does Newport Green FITC-Gly-Gly-His, FITC-Gly-His, for Cu$^{2+}$ and Hg$^{2+}$ Phen Green for Cut and Phen Green for Fe$^{2+}$, Cu$^{2+}$, Cu$^+$, Hg$^{2+}$, Pb$^{2+}$, Cd$^{2+}$, Zn$^{2+}$, and Ni$^{2+}$. Chelating agents and fluorescent chelating agents for other ions, such as aluminum, cadmium, potassium, sodium, magnesium, bromide, and chloride ions can be found, for example, in Haugland, ed., *Handbook of Fluorescent Probes and Research Chemicals,* 6th ed., 1996, published by Molecular Probes, Eugene, Oregon. Still another suitable doping material is one whose fluorescence or absorption is affected by changes in pH. Two such compounds are fluorescein, SNARF, SNAFL, 8-hydroxypyrene-1,3,6-trisulfonic acid, DM-NERF and CL-NERF (available from Molecular Probes. Still other suitable doping/sensing agents include fluorescently labeled nucleic acids as DNA and RNA probes and solvatochromic choromophores and/or fluorophores for monitoring solvent purity.

Furthermore, the present invention has been illustrated using a housing having an inlet and an outlet. This configuration is particularly well suited where the sample is gaseous. However, the invention can be practiced using any suitable housing, including containers having only one opening, such as a beaker. Alternatively, the method can be practiced without the use of any housing, for example, to quantify the presence of oxygen in ambient air. In the latter case, for accurate results, the light source and detector are preferably maintained at a fixed distance from one another by some suitable means that would be readily apparent to those of ordinary skill in the art.

Having thus described the basic concept of the invention, it will be rather apparent to those skilled in the art that the foregoing detailed disclosure is intended to be presented by way of example only, and is not limiting. Various alternations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

REFERENCES

1. I. Bergman, Nature 218,396 (1968).
2. H. Kroneis and H. J. Marsoner, Sensors Actuators 4, 587 (1983).
3. A. Sharma and O. S. Wolfbeis, Appl. Spectrosc. 42, 1009 (1988).
4. J. I. Peterson, R. V. Fitzgerald, and D. K. Buckhold, Anal. Chem. 56, 62 (1984).
5. O. S. Wolfbeis, H. E. Posch, and H. Kroneis, Anal. Chem. 57, 2556 (1985).
6. S-K. Lee and I. Okura, Analyst 122, 81 (1997).
7. D. B. Papkovsky, Sensors Actuators B 29, 213 (1995).
8. I. Klimant, P. Belser, and O. S. Wolfbeis, Talanta 41, No. 6, 985 (1994).
9. W. Xu, R. C. McDonough, B. Langsdorf, J. N. Demas, and B. A. DeGraff, Anal. Chem. 66, 4133 (1994).
10. J. R. Bacon and J. N. Demas, Anal. Chem. 59, 2780 (1987).
11. W. Xu, R. Schmidt, M. Whaley, J. N. Demas, B. A. DeGraff, E. K. Karikari, and B. A. Farmer, Anal. Chem. 67, 3172 (1995).
12. S. Draxler and M. E. Lippitsch, Appl. Opt. 35, 4117 (1996).
13. K. E. Chung, E. H. Lan, M. S. Davidson, B. S. Dunn, J. S. Valentine, and J. I. Zink, Anal. Chem. 67, 1505 (1995).
14. P. Hartmann, M. J. Leiner, and M. E. Lippitsch, Anal. Chem. 67, 88 (1995).
15. I. Klimant and O. S. Wolfbeis, Anal. Chem. 67, 3160 (1995).
16. L. Sacksteder, J. N. Demas, and B. A. DeGraff, Anal. Chem. 65 3480 (1993).
17. B. D. MacCraith, G. O'Keefe, A. K. McEvoy, C. M. McDonagh, J. F. McGilp, B. O'Kelly, J. D. O'Mahony, and M. Cavanagh, Opt. Eng. 33, 3861 (1994).
18. B. D. MacCraith, G. O'Keefe, C. McDonagh, and A. K. McEvoy, Electron. Lett. 30, 888 (1994).
19. M. K. Krihak and M. R. Shahriari, Electron. Lett. 32, 240 (1996).
20. M. T. Murtagh, D. E. Ackley, and M. R. Shahriari, Electron. Lett. 32, 477 (1996).
21. A. K. McEvoy, C. M. McDonagh, and B. D. MacCraith, Analyst 121, 785 (1996).
22. E. R. Carraway, J. N. Demas, B. A. DeGraff, and J. R. Bacon, Anal. Chem. 63, 337 (1991).
23. J. N. Demas, E. W. Harris, and R. P. McBride, J. Am. Chem. Soc. 93, 3184 (1971).
24. S. Buell and J. N. Demas, J. Phys. Chem. 87, 4675 (1983).
25. J. R. Lakowicz, *Principles of Fluorescence Spectroscopy* (Plenum Press, New York, 1983), Chap. 9.
26. M. R. Eftink, "Fluorescence Quenching: Theory and Applications", in *Topics in Fluorescence Spectroscopy*, J. R. Lakowicz, Ed. (Plenum Press, New York, 1991), Vol. 2, Chap. 2.
27. C-T. Lin, W. Bottcher, M. Chou, C. Creutz, and N. Sutin, J. Am. Chem. Soc. 98, 6536 (1976).
28. K. Mandal, T. D. L. Pearson, and J. N. Demas, Anal. Chem. 20, 786 (1981).
29. J. N. Demas and B. A. DeGraff, J. Chem. Ed. 74, 690 (1997).
30. C. M. Ingersoll and F. V. Bright, CHEMTECH 27, 26 (1997).
31. O. Lev, M. Tsionsky, L. Rabinovich, V. Gelzer, S. Sampath, I. Pankratov, and J. Gun, Anal. Chem. 67, 22A (1995).
32. B. C. Dave, B. Dunn, J. S. Valentine, and J. I. Zink, Anal Chem. 66, 1120A (1994).
33. P. W. Atkins, *Physical Chemistry* (W. H. Freeman and Company, New York, 1990), $4^{th}$ ed., Chap. 7.

What is claimed is:

1. A sensing system for quantifying an analyte in a sample comprising:
    a light source coupled to a power source, the light source comprising:
        a housing having a transparent portion and
        a light emitter contained within the housing;
    a sol-gel-derived film deposited directly and at least partially on the transparent portion of the housing, the sol-gel-derived film being doped with a doping material; and
    a detector that is substantially across and separated by an open space from the transparent portion of the housing which is at least partially coated with the sol-gel-derived film.

2. The sensing system as set forth in claim 1, wherein the sol-gel-derived film comprises a polymerization product of a tetraalkoxysilane or mixture of alkyl- or alkoxysilane.

3. The sensing system as set forth in claim 1, wherein the sol-gel-derived film comprises a polymerization product of a composition comprising tetraethoxysilane, ethanol, water, and a mineral acid in molar ratios of about $1:2:2:10^{-4}$.

4. The sensing system as set forth in claim 1, wherein the doping material is capable of absorbing light from the light source or fluorescing when excited by light from the light source and wherein the analyte, when contacted with the doping material, is capable of affecting the doping material's ability to absorb light from the light source or to fluoresce when excited by light from the light source.

5. The sensing system as set forth in claim 1, wherein the doping material is selected from the group consisting of a ruthenium complex, a fluorescent or light absorbing oxidase enzyme or antibody specific for the analyte, a fluorescent or light absorbing chealator, cryptand, or host specific for the analyte, fluorescein, and other pH sensitive chromophores or fluorophores.

6. The sensing system as set forth in claim 5, wherein the ruthenium complex is $[Ru(dpp)_3]^{2+}$.

7. The sensing system as set forth in claim 1, wherein the light source comprises a light emitting diode.

8. The sensing system as set forth in claim 1, wherein the detector comprises a photodiode.

9. The sensing system as set forth in claim 1 further comprising:

a filter located between the light source and the detector; and a processing system coupled to the detector for processing data detected by the detector to quantify the amount of analyte in the sample.

10. The sensing system as set forth in claim 1 further comprising:

a housing with an inlet and an outlet, wherein the light source and detector are located between the inlet and the outlet and wherein the light source is substantially across and separated by an open space from the detector.

11. The sensing system according to claim 1 wherein there is no optical fiber between the housing and the deposited sol-gel-derived film.

12. A sensing apparatus comprising:

a first housing with an inlet for receiving a sample and an outlet for discharging the sample;

a light source coupled to a power source, the light source being positioned in the first housing between the inlet and the outlet and comprising;

a second housing having a transparent portion and a light emitter contained within the second housing;

a sol-gel-derived film deposited directly and at least partially on the transparent portion of the second housing, the sol-gel-derived film being doped with a doping agent; and a detector located in the housing substantially across and separated by an open space from the transparent portion of the second housing which is at least partially coated with the sol-gel-derived film.

13. The sensing apparatus as set forth in claim 12, wherein the sol-gel-derived film comprises a polymerization product of a tetraalkoxysilane or mixture of alkyl- or alkoxysilane.

14. The sensing apparatus as set forth in claim 12, wherein the sol-gel-derived film comprises a polymerization product of a composition comprising tetraethoxysilane, ethanol, water, and a mineral acid in molar ratios of about $1:2:2:10^{-4}$.

15. The sensing apparatus as set forth in claim 12, wherein the doping material is capable of absorbing light from the light source or fluorescing when excited by light from the light source and wherein the analyte, when contacted with the doping material, is capable of affecting the doping material's ability to absorb light from the light source or to fluoresce when excited by light from the light source.

16. The sensing apparatus as set forth in claim 12, wherein the doping material is selected from the group consisting of a ruthenium complex, a fluorescent or light absorbing oxidase enzyme or antibody specific for the analyte, a fluorescent or light absorbing chealator, cryptand, or host specific for the analyte, fluorescein, and other pH sensitive chromophores or fluorophores.

17. The sensing apparatus as set forth in claim 16, wherein the ruthenium complex is $[Ru(dpp)_3]^{2+}$.

18. The sensing apparatus as set forth in claim 12, wherein the light source comprises a light emitting diode.

19. The sensing apparatus as set forth in claim 12, wherein the detector comprises a photodiode.

20. The sensing apparatus as set forth in claim 12 further comprising:

a filter located between the light source and the detector; and a processing system coupled to the detector for processing data detected by the detector.

21. The sensing apparatus according to claim 11 wherein there is no optical fiber between the second housing and the deposited sol-gel-derived film.

* * * * *